US00PP15764P3

(12) United States Plant Patent

Kanaya et al.

(10) Patent No.: US PP15,764 P3
(45) Date of Patent: May 17, 2005

(54) *CALIBRACHOA* PLANT NAMED 'SUNBELHO'

(50) Latin Name: ***Calibrachoa* sp.**
Varietal Denomination: Sunbelho

(75) Inventors: Takeshi Kanaya, Omihachiman (JP); Yasuyuki Murakami, Gamo-gun (JP)

(73) Assignee: Suntory Flowers Limited, Tokyo (JP)

( * ) Notice: Subject to any disclaimer, the term of this patent is extended or adjusted under 35 U.S.C. 154(b) by 25 days.

(21) Appl. No.: 10/650,460

(22) Filed: Aug. 28, 2003

(65) Prior Publication Data

US 2005/0050605 P1 Mar. 3, 2005

(51) Int. Cl.[7] ..... A01H 5/00
(52) U.S. Cl. ..... Plt./263
(58) Field of Search ..... Plt./263, 356

(56) References Cited

U.S. PATENT DOCUMENTS

| | | | |
|---|---|---|---|
| PP9,557 | P | 5/1996 | Suzuki et al. |
| PP9,754 | P | 12/1996 | Suzuki et al. |
| PP10,278 | P | 3/1998 | Murakami |
| PP10,355 | P | 4/1998 | Murakami |
| PP11,558 | P | 10/2000 | Murakami |

FOREIGN PATENT DOCUMENTS

| | | |
|---|---|---|
| JP | PBR 7232 | 6/1999 |
| JP | PBR 7391 | 9/1999 |

OTHER PUBLICATIONS

Catalog: *Flower & Green*, 2003, published by Suntory Flowers Limited, p. 14 (4 pp), Partial English translation of p. 14.

Catalog: *The 2004 Suntory Collection*, published by Jackson & Perkins Wholesale, Inc., p. 7 (3pp).

Catalog: *Pineae Peak Performers featuring the 2004 Suntory Collection*, published by Pineae Greenhouses, pp. 6 and 7 (4pp).

*Primary Examiner*—Kent Bell
(74) *Attorney, Agent, or Firm*—Christie, Parker and Hale, LLP

(57) ABSTRACT

Disclosed herein is a new and distinct variety of *Calibrachoa* plant, having a semi-decumbent habit. The *Calibrachoa* plant has abundant branching particularly with respect to secondary branching, and a great profusion of blooms with the entire plant remaining in bloom for a considerable period of time. the flowers are single and very small with the white petals. the base color of the corolla throat is brilliant greenish yellow and the outside of the corolla tube is brilliant greenish yellow. The plant exhibits high resistance to rain, heat, drought and diseases such as powdery mildew.

2 Drawing Sheets

Botanical/commercial classification: *Calibrachoa* sp.
Varietal denomination: cv. 'Sunbelho'.

BACKGROUND OF THE VARIETY

The *Calibrachoa* is a very popular plant that is used for flower bedding and potting in the summer season. There are only a few *Calibrachoa* having small flowers, currently classified as *Calibrachoa,* such as 'Suntory SP-R' (U.S. Plant Pat. No. 9,557), 'Sunberubu' (U.S. Plant Pat. No. 9,754, 'Sunbelchipi' (U.S. Plant Pat. No. 10,355) and 'Sunbelki' (U.S. Plant Pat. No. 11,558). These are of the semi-decumbent type, a medium plant height, abundant, branching, and a high resistance to heat and rain and disease.

The new variety of *Calibrachoa* plant according to this invention originated from crossing with the *Calibrachoa* variety called '9W16' and the other *Calibrachoa* plant variety called '9W6'.

First of all, a crossing was conducted with the '9W16' variety as female parent and a *Calibrachoa* plant variety '9W6' as pollen parent in April 1998 at 863-1, Aza-Iketani, Omori-cho, Yokaichi-shi, Shiga-ken, Japan. From that crossing 50 seedlings were obtained and 5 seedlings were selected in view of their semi-erect growth habit by the end of September 1999. These 5 seedlings were grown and were tested during potting and bedding trials. Only one plant was selected in September 2000. The selected plant was propagated by cutting and then grown in pot on trial in the green house and the field at 863-1, Aza-Iketani, Omori-cho, Yokaichi-shi, Shiga-ken, Japan from April to October 2001. The botanical characteristics of the finally selected plant were examined, using similar variety 'Sunbelchipi' (U.S. Plant Pat. No. 10,355) for comparison. As a result, it was concluded that this new *Calibrachoa* is distinguishable from any other variety, whose existence is known to us, and is uniform and stable in its characteristics. This new variety of *Calibrachoa* plant was named 'Sunbelho'.The new variety reproduces true to type in successive generations of asexual reproduction.

In the following description, the color information is in accordance with The R.H.S. Colour Chart of The Royal Horticultural Society, London, England. A color chart based on The Japan Color Standard for Horticultural Plants (J.H.S. Color Chart) is also added for reference.

The '9W16', used as female parent in the obtaining of this new variety 'Sunbelho', is our bred variety previously filed in Japan. The main botanical characteristics of the '9W16' are as follows:

Plant:

*Growth habit.*—Semi-decumbent.
*Plant height.*—18 cm.
*Spreading area of plant.*—Slightly large.
*Blooming period.*—April to late October in the southern Kanto area, Japan. The plant shape does not change throughout this period.

Stem:
*Thickness.*—2.8 mm.
*Pubescence.*—Sparse.
*Branching.*—Abundant with the superior branching propensity, especially secondary branches are.
*Length of internode.*—2.2 cm.
Leaf:
*Shape.*—Semi-lanceolate.
*Length.*—5.2 cm.
*Width.*—2.2 cm.
*Color.*—Dark yellow green (R.H.S. 146A, J.H.S. 3508).
*Thickness.*—0.3 mm.
*Pubescence.*—Sparse.
*Leaf attaching angle to stem.*—Horizontal.
Flower:
*Facing direction.*—Slantly upward.
*Type.*—Single.
*Shape.*—Funnel-shape with five-fissured limb.
*Shape of petal tip.*—Slightly acute.
*Waving of petal.*—Weak.
*Lobation of petal.*—Shallow.
*Diameter.*—2.9 cm.
*Color.*—Petal: Vivid red purple R.H.S. 74A, J.H.S. 9207). Bottom color of corolla throat: light greenish yellow (R.H.S. 5D, J.H.S. 2703). Outside color of corolla tube: Bright greenish yellow (R.H.S. 5C, J.H.S. 2905).
*Reproductive organs.*—1 normal pistil and 5 normal stamens.
*Fertility.*—Fertile, but self-incompatible.
*Peduncle.*—1.3 mm in thickness, and 2.3 cm in length.
*Physiological and ecological characteristics.*—High resistance to cold, heat, rain and diseases, such as powdery mildew. The resistance to heat and rain is very strong.
Blooming: A bloom commonly lasts approximately 10 days on the plant. Pinching in not necessary to ensure continuous blooming; however, it does tend to enhance bloom production.

The '9W6', used as male parent in the obtaining of this new variety 'Sunbelho', is our bred variety and not filed in Japan nor any other country. '9W6' had been grown in Yokaichi-shi, Shiga-ken, Japan. The main botanical characteristics of the '9W6' are as follows:

Plant:
*Growth habit.*—Semi-erect.
*Plant height.*—26 cm.
*Spreading area of plant.*—Slightly large.
*Blooming period.*—April to late October in the southern Kanto area, Japan. The plant shape does not change throughout this period.
Stem:
*Thickness.*—2.2 mm.
*Pubescence.*—Normal.
*Branching.*—Abundant with the superior branching propensity, especially secondary branches are.
*Length of internode.*—1.7 cm.
Leaf:
*Shape.*—Lanceolate.
*Length.*—4.8 cm.
*Width.*—1.3 cm.
*Color.*—Dark yellow green (R.H.S. 146A, J.H.S. 3508).
*Thickness.*—0.3 mm.
*Pubescence.*—Sparse.
*Leaf attaching angle to stem.*—Horizontal.
Flower:
*Facing direction.*—Slantly upward.
*Type.*—Single.
*Shape.*—Funnel-shape, with five-fissured limb.
*Shape of petal tip.*—Slightly acute.
*Waving of petal.*—Weak.
*Lobation of petal.*—Shallow.
*Diameter.*—3.1 cm.
*Color.*—Petal: Vivid red purple (R.H.S. 61C, J.H.S. 9507). Bottom color of corolla throat: Strong greenish yellow (R.H.S. 4C, J.H.S. 2707). Outside color of corolla tube: Pale greenish yellow (R.H.S. 5D, J.H.S. 2703).
*Reproductive organs.*—1 normal pistil and 5 normal stamens.
*Fertility.*—Fertile, but self-incompatible.
*Peduncle.*—1.2 mm. in thickness, and 1.6 cm in length.
*Physiological and ecological characteristics.*—High resistance to cold, heat, rain and diseases such as powdery mildew. The resistance to heat and rain is very strong.
Blooming: A bloom commonly lasts approximately 10 days on the plant. Pinching is not necessary to ensure continuous blooming; however, it does tend to enhance bloom production.

The 'Sunbelchipi', used as a comparison in the obtaining of this new variety 'Sunbelho' is our bred variety previously filed in Japan (Seeds and Seedlings Law Registration No. 7232) and U.S.A. (U.S. Plant Pat. No. 10,355). The main botanical characteristics of the 'Sunbelchipi' are as follows:

Plant:
*Growth habit.*—Semi-decumbent.
*Plant height.*—16 cm.
*Spreading area of the plant.*—Slightly large.
*Blooming period.*—April to late October in the southern Kanto area, Japan. The plant shape does not change throughout this period.
Stem:
*Thickness.*—2.4 mm.
*Pubescence.*—Normal.
*Branching.*—Abundant with the superior branching propensity, especially secondary branches are.
*Length of internode.*—2.1 cm.
Leaf:
*Shape.*—Lanceolate.
*Length.*—5.2 cm.
*Width.*—1.4 cm.
*Color.*—Dark yellow green (R.H.S. 146A, J.H.S. 3508).
*Thickness.*—0.4 mm.
*Pubescence.*—Sparse.
*Leaf attaching angle to stem.*—Horizontal to slightly droopy.
Flower:
*Facing direction.*—Horizontal.
*Type.*—Single.
*Shape.*—Funnel-shape, with five-fissured limb.
*Shape of petal tip.*—Medium.
*Waving of petal.*—Weak.
*Lobation of petal.*—Shallow.
*Diameter.*—2.9 cm.

*Color.*—Petal: Vivid purplish red (R.H.S. 57C, J.H.S. 9707. Bottom color of corolla throat: Strong yellow (R.H.S. 9A, J.H.S. 2513). Outside color of corolla tube: Light greenish yellow (R.H.S. 5C, J.H.S. 2904).

*Reproductive organs.*—1 normal pistil and 5 normal stamens.

*Fertility.*—Fertile, but self-incompatible.

*Peduncle.*—0.8 mm in thickness, and 2.0 cm in length.

*Physiological and ecological characteristics.*—High resistance to cold, heat, rain and diseases such as powdery mildew. The resistance to heat and rain is very strong.

Blooming: A bloom commonly lasts approximately 10 days on the plant. Pinching is not necessary to ensure continuous blooming; however, it does tend to enhance bloom production.

SUMMARY OF THE VARIETY

This new variety of *Calibrachoa* plant 'Sunbelho' has a semi-decumbent growth habit with abundant branching, with single and very small white color flowers and forms a great profusion of blooms with the whole plant remaining in bloom for a considerable period of time. The plant is highly tolerant to cold, rain, heat and diseases, particularly powdery mildew and highly resistance to heat and rain.

BRIEF DESCRIPTION OF THE PHOTOGRAPH

DESCRIPTION OF THE NEW VARIETY

Figure 1:
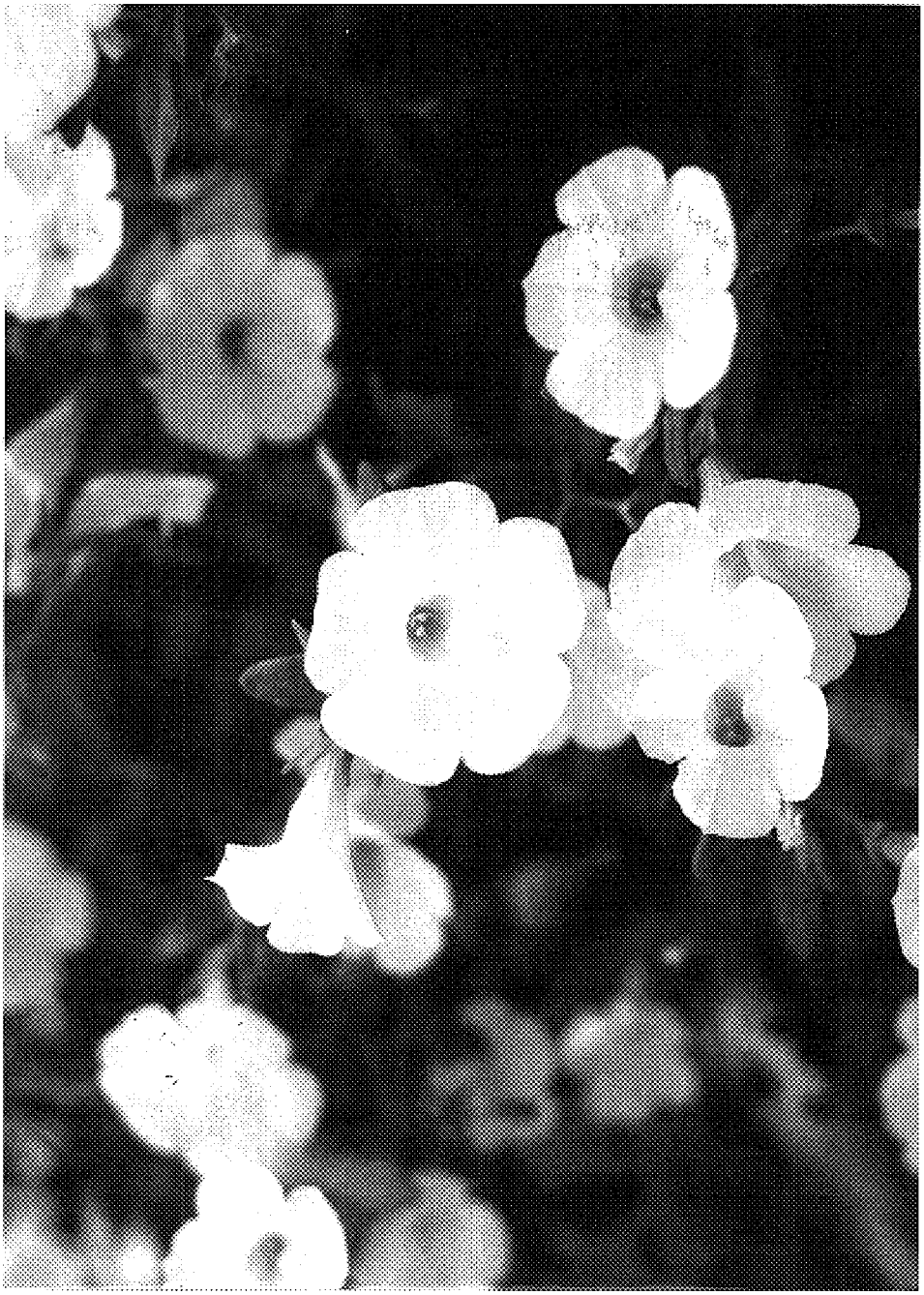
FIG. 1 is a photograph of flowers and leaves of the new variety of *Calibrachoa* plant 'Sunbelho'.
Figure 2:
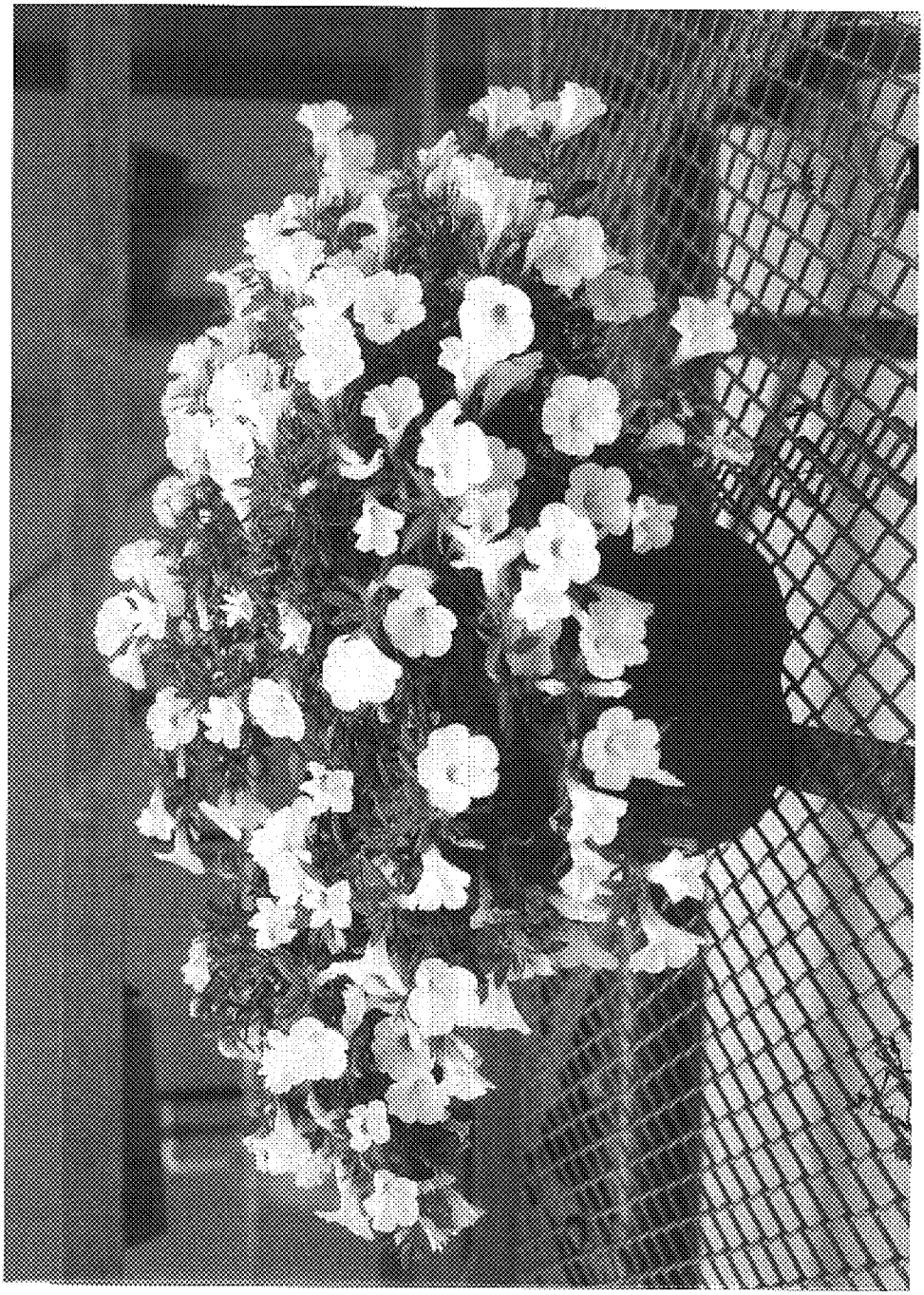
FIG. 2 is a photograph of a typical plant of the new variety of *Calibrachoa* plant 'Sunbelho' growing in a pot.

The botanical characteristics of the new and distinct variety of *Calibrachoa* plant named 'Sunbelho' are as follows when observing during October at Yokaichi-shi, Shiga-ken, Japan, young plants that had been reproduced by cuttings in June.

Plant:

*Growth habit.*—Semi-decumbent.

*Plant height.*—Approximately 16 cm.

*Spreading area of plant.*—Approximately 35 cm.

*Blooming period.*—April to late October in the southern Kanto area, Japan. The first flower would be observed approximately four weeks after planting. The plant shape does not change throughout this period.

Stem:

*Thickness.*—Approximately 2.3 mm.

*Length.*—Approximately 18 cm.

*Color.*—Near R.H.S. 144A.

*Pubescence.*—Normal.

*Branching.*—Abundant with the superior branching propensity, especially secondary branches are.

*Length of internode.*—Approximately 2.6 cm.

Leaf:

*Shape.*—Lanceolate.

*Length.*—Approximately 5.1 cm.

*Width.*—Approxiamtely 1.6 cm.

*Color.*—Upper — Dark yellow green (near R.H.S. 146A, J.H.S. 3508). Lower — near R.H.S. 146B.

*Thickness.*—Approximately 0.4 mm.

*Pubescence.*—Sparse.

*Apex.*—Obtuse.

*Margin.*—Entire.

*Base shape.*—Cuneate.

*Leaf attaching angle to stem.*—Horizontal to slightly droopy.

Flower:

*Facing direction.*—Slantly upward to horizontal.

*Type.*—Single.

*Bud shape.*—Lenticular.

*Bud length.*—Approximately 2.0 cm.

*Bud diameter.*—Approximately 0.5 cm.

*Bud color.*—Near R.H.S. 145C.

*Shape.*—Funnel-shape, with five petals.

*Apex shape of petal.*—Truncate.

*Petal margin.*—Entire.

*Shape of petal tip.*—Medium.

*Waving of petal.*—Weak.

*Diameter of entire flower.*—Approximately 3.0 cm.

*Height of flower.*—Approximately 3.0 cm. Petals are fused at the base and the petal length from the throat is approximately 1.5 cm, the petal width is approximately 1.5 cm, the length of the corolla tube is approximately 1.5 cm and the flower throat diameter is approximately 0.7 cm.

*Color.*—Petal (both upper the lower sides): White (near R.H.S.155A, J.H.S. -01). Bottom color of corolla throat: Brilliant greenish yellow (near R.H.S. 8A, J.H.S. 2704). Inside color of corolla throat: near R.H.S. 8A with vein near R.H.S. 145B. Outside color of corolla tube: Bright greenish yellow (near R.H.S. 5C, J.H.S. 2905). Outside color of corolla throat is near R.H.S. 5C with vein near R.H.S. 145B.

*Fragrance.*—None.

Sepal:

*Number.*—5; fused at base.

*Sepal length.*—Approximately 1.0 cm.

*Sepal width.*—Approximately 2.0 mm.

*Apex shape.*—Acute.

*Margin.*—Entire.

*Color.*—Inside sepal color near R.H.S. 146A and outside sepal color near R.H.S. 144A.

*Reproductive organs.*—1 normal pistil and 5 normal stamens.

*Fertility.*—Fertile, but self-imcompatible.

*Peduncle.*—Approximately 0.8 mm in thickness, and approximately 1.9 cm in length. Color is near R.H.S. 144A.

Physiological and ecological characteristics.—High resistance to cold, heat, rain and diseases such as powdery mildew. The resistance to heat and rain is very strong. The USDA Hardiness Zones of the instant variety is No. 9.

Pest resistance/susceptibility: No serious damage by white fly or aphids has been observed.

Blooming: A bloom commonly lasts approximately 10 days on the plant. Pinching is not necessary to ensure continuous blooming; however, it does tend to enhance bloom production.

This new variety of *Calibrachoa* plant is most suitable for flower bedding and potting, particularly in hanging pots or planters, and is excellent for use as ground cover. Pinching of old blossoms will enhance the formation of new blossoms.

What is claimed is:

1. A new and distinct variety of *Calibrachoa* plant named 'Sunbelho', substantially as herein illustrated and described.

* * * * *